United States Patent [19]

Lenkauskas

[11] Patent Number: 4,957,507
[45] Date of Patent: Sep. 18, 1990

[54] WIRE SPRING PROSTHESIS FOR OSSICULAR RECONSTRUCTION

[76] Inventor: Edmundas Lenkauskas, 3024 Kersdale Rd., Pepper Pike, Ohio 44124

[21] Appl. No.: 132,782

[22] Filed: Dec. 14, 1987

[51] Int. Cl.⁵ .............................................. A61F 2/18
[52] U.S. Cl. ...................................................... 623/10
[58] Field of Search .............................. 623/10, 11, 16; 626/275, 155, 180

[56] References Cited

U.S. PATENT DOCUMENTS

| | | | |
|---|---|---|---|
| 1,470,583 | 10/1923 | Messenger | 267/155 |
| 1,627,220 | 5/1927 | Withrow | 267/275 |
| 1,633,695 | 6/1927 | Colbey | 267/155 |
| 3,606,525 | 9/1971 | Landree | 267/155 |
| 3,751,025 | 8/1973 | Beery et al. | 267/180 |
| 3,987,789 | 10/1976 | Timm et al. | 623/10 |
| 4,397,453 | 8/1983 | Seecamp | 267/100 |
| 4,601,723 | 7/1986 | McGrew | 623/10 |
| 4,624,672 | 11/1986 | Lenkauskas | 263/10 |
| 4,641,651 | 2/1987 | Card | 623/10 |
| 4,678,970 | 7/1987 | Nashef et al. | 623/16 |

FOREIGN PATENT DOCUMENTS 542482 8/1922 France ................................. 267/275

*Primary Examiner*—David J. Isabella
*Attorney, Agent, or Firm*—Vytas R. Matas

[57] ABSTRACT

A compact and highly flexible spring wire prosthestic device is provided for ossicular reconstruction. This prosthesis provides a solution not only to probelms associated with lateral retraction of the Tympanic graft and slippage of the prosthesis but to some other ossiculoplasty problems as well. The device has an oval shaped spring member locatable between the tympanic membrane and the footplate of the stapes with the major axis or diameter substantially parallel to the tympanic membrane making the device easily mountable. Obliquely extending from the oval spring member is an arm terminating in an ampersand shaped member for connecting the device to the tympanic membrane when the handle of the malleus is still present. Where there is no malleus handle, the prosthesis is provided with a freely mobile biocompatible disc equally distributing the tension pressure to the undersurface of the tympanic membrane. The spring also acts as a shock absorber. The wire of the device is formed from a plurality of wire strands twisted together into a cable of high tensile strength and great flexibility.

13 Claims, 4 Drawing Sheets

WIRE SPRING PROSTHESIS FOR OSSICULAR RECONSTRUCTION

BACKGROUND OF THE INVENTION

1. Field of the Invention

The present invention relates to otic wire spring prosthesis in general and in particular to a middle ear prosthesis used in ossicular reconstruction 2. Description of the Prior Art It is presently known to repair the sound conducting mechanism of the middle ear by surgical implantation of various types of prosthesis. Such repair may involve either total reconstruction where all three ossicles between the tympanic membrance and the oval window of the inner ear are replaced by a prosthesis, partial reconstruction wherein only the malleus and the incus or only the incus is replaced.

Known prior art prosthesis for reconstruction procedures have been made from various natural materials such as cartilage and bone, and from various man-made materials such as stainless steel and plastics like Teflon, Polyethelene, and Bio-compatible materials like Proplast and Plastipore New ceramics are also being developed such as Ceravital and Hydroxapatite.

Irrespective of the material most of the prosthetic devices known are usually one piece straight shaft devices having a head portion resting against the tympanic membrane with the opposite end pressing against the footplate of the stapes for complete reconstruction procedures or the stapes capitulum-superstructure for partial reconstruction procedures.

For a discussion of prior art prosthetic devices and the implanting techniques of same, the reader is referred to the following articles which discuss such devices in greater detail. These articles are (1) "BIOCOMPATIBLE OSSICULAR IMPLANTS" by John J. Shea, M.D. and John R. Emmett, M.D. appearing in Volume 104, April 1978, Issue of Arch. Otolaryngol; (2) "A DECADE OF TYMPANOPLASTY: PROGRESS OR REGRESS?" by David F. Austin, M.D. appearing in the May 1982 Issue of Larynogoscope 92; (3) "OSSICULAR CHAIN RECONSTRUCTION: THE TORP AND PORP AND CHRONIC EAR DISEASE" by C. Gary Jackson, M.D. et al appearing in the Aug. 1983 Issue of Larynogoscope; (4) BIOACTINE GLASS - CERAMIC IN EAR SURGERY: AUINIAL STUDIES AND CLINICAL RESULTS by Reck, R. appearing in February, 1984 Issue of Larynogoscope (Suppl. 33); and (5) RECONSTRUCTION OF THE OSSICULAR CHAIN WITH HYDROXAPATITE INPLANTS by J. Grote appearing in Annals of Otology Rhinology and Laryngology (Suppl. 123), Volume 95, March - April 1986.

Wire prosthetic devices are also known. Some such devices consist of a straight shaft stainless steel wire with a transverse bar located at one end of the wire shaft. The bar or any other transverse section is intended to limit the insertion of the device into any base material such as cartilage located under the tympanic membrane. All straight shaft prosthetic devices give rise to certain problems due to their lack of flexibility. Slight outward retraction and/or shift of the tympanic membrane which may occur during the post-operative healing process causes the tip of the prosthetic device to lift off or slip from either the footplate or stapes head, depending upon the type of reconstruction, resulting in a loss of the tension pressure between the tympanic membrane and the footplate initially set by the surgeon implanting the prosthetic device. As a result, the patient does not hear as well after healing from the operation as he did when the operation was just performed. When the ear is subjected to a loud noise, the extreme deflection of the tympanic membrane caused by the noise may damage the inner ear—the cochlea. Also, with a straight shaft prosthesis there is no protection for inner ear damage from external physical trauma to the ear.

Coil spring wire prosthesis such as may be found in U.S. Pat. No. 4,624,672 issued to the present Applicant Edmundas Lenkauskas M.D., provides flexibility to absorb shocks induced by loud noises or other external trauma to the ear. They also have sufficient flexibility to compensate for any displacement change between the tympanic membrane and the inner ear due to outward retraction occurring during the post operative healing process to maintain sufficient pressure between them to insure adequate hearing restoration over an extended period of time. However, such prosthesis have relatively large central coil to provide such flexibility. This requires an accurate installation technique into the middle ear space to prevent the touching of the coil to the walls of the middle ear or promontory which may cause a short circuiting of the sound energy. Also such prostheses did not have the ability in the prosthesis head to adjust to positional variances of the tympanicmembrane. Thus equal distribution of pressure to the undersuface of the tympanic membrane was not provided.

SUMMARY OF THE INVENTION

The present invention overcomes the mentioned problems associated with the known prior art devices as well as other problems by providing a compact but high flexible wire-prosthetic device useful for ossicular replacement procedures. The device is formed to have a centrally located oval shaped spring member between a pair of leg members with the oval formed to be enclosed between the narrower separation of the leg members forming an enclosed angle therebetween thus placing the oval along the length of the leg members of the prosthesis wherein the major axis of the oval member extends substantially parallel to the tympanic membrane but is spaced therefrom. The oval spring member is located midway between the footplate and the tympanic membrane so that sufficient space is maintained between the oval spring member and the primintory of the middle ear to prevent any short circuiting of the vibrations (sound energy).

In one particular embodiment of the device, the entire wire spring-prosthesis if formed from a twisted wire assembly which is made up of three individual wire strands twisted together into a single unit. This twisted wire unit provides high flexibility to the prosthesis as well as compact size while retaining the requisite tensile strength. The high flexibility allows a compact form to the oval spring member ensuring sufficient space for the prosthesis within the middle ear.

In another embodiment of the device, a wire arm extends obliquely from the oval spring member towards the tympanic membrane. In situations where the tympanic membrane still retains a malleus handle, the end of the wire arm is formed as an ampersand shaped member which is used to connect the tympanic membrane to the prosthesis. The malleus handle is captured into the open end of the ampersand shaped member. The ampersand shaped member thus captures the malleus within itself under pressure and prevents any dislodging of the prosthesis. In situations where a malleus handle is lacking, a biocompatible disc member is loosely tied to the end of the wire arm member which is formed to have a closed loop. The disc has a central opening which contains a bone chip. This bone chip is pressed against the tympanic membrane preventing the disc from sliding along the tympanic membrane by the lodging of the bone chip into the tympanic membrane.

In view of the foregoing, it will be seen that one aspect of the Applicant's present invention is to provide a highly flexible yet compact spring wire prosthesis.

Yet another aspect of the Applicant's present invention is to provide a wire prosthesis which is inherently flexible yet having a high tensile strength due to the twisting of a plurality of wires into a single unit.

Still yet another aspect of the Applicant's present invention is to provide a positive structure for connecting the prosthesis to the tympanic membrane.

These and other aspects of the Applicant's present invention will become more apparent upon a review of the following description of the preferred embodiment when considered in conjunction with the accompanying drawings.

DETAILED DESCRIPTION OF THE PREFERRED EMBODIMENT

Figure 1:
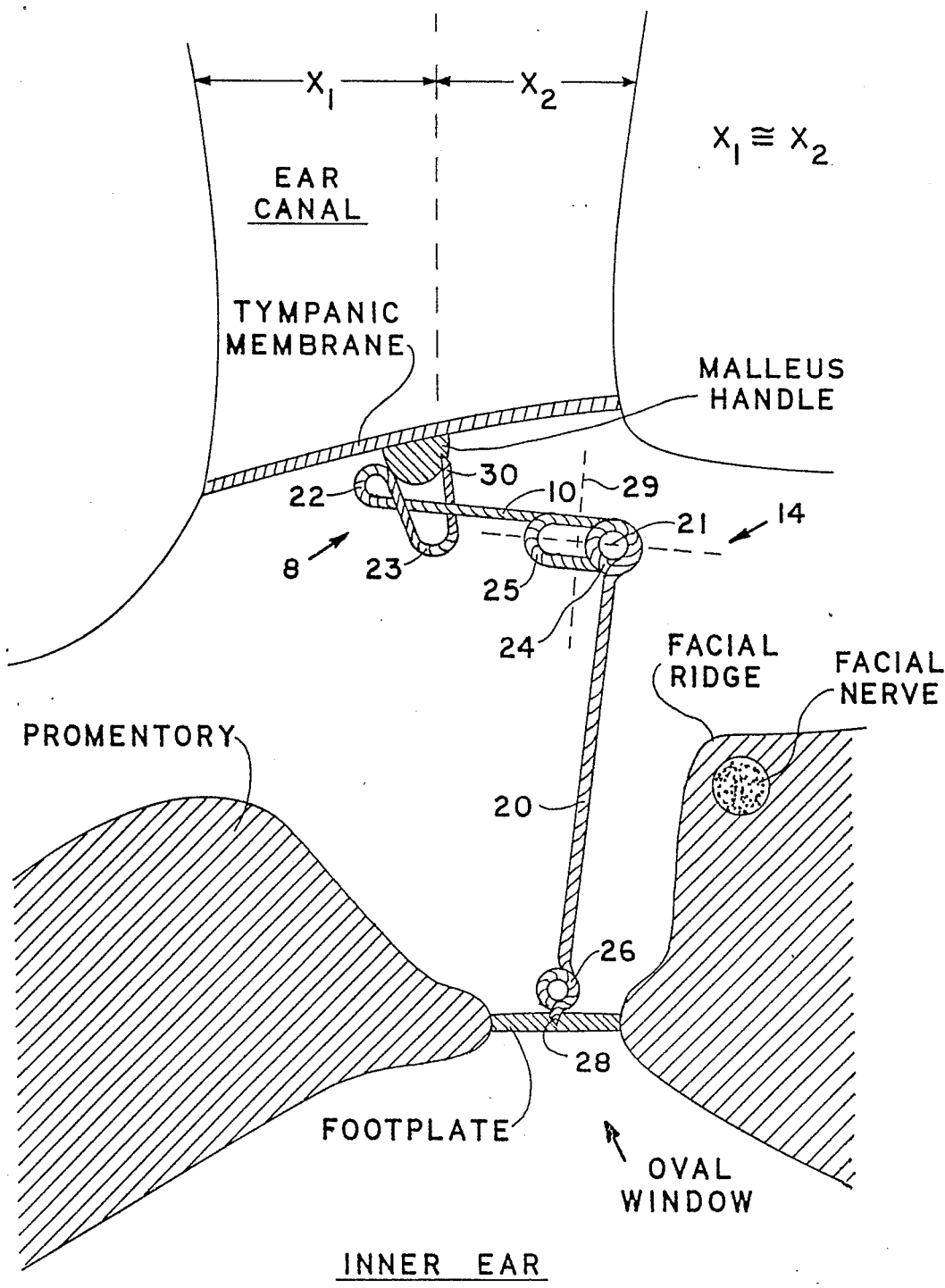
FIG. 1 shows the present spring wire prosthesis connected to the tympanic membrane by way of the malleus handle.
Figure 2:
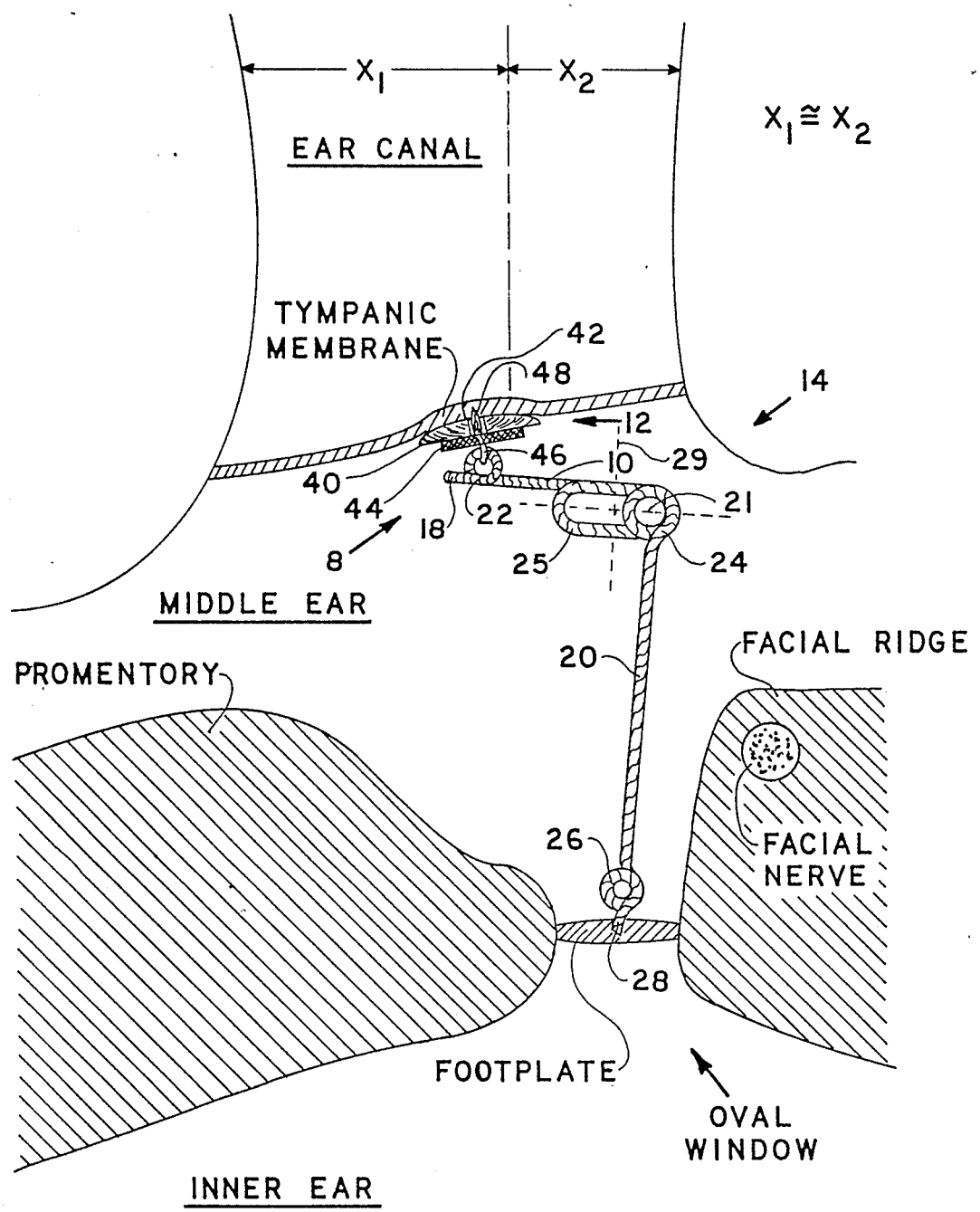
FIG. 2 shows an alternate embodiment of the FIG. 1 prosthesis wherein the prosthesis is connected to the tympanic membrane by way of a biocompatible disc with a bone chip tied to one end of the prosthesis.
Figure 3:
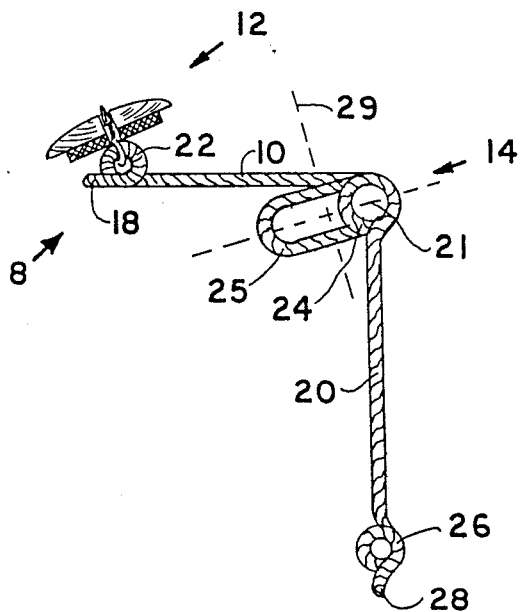
FIG. 3 shows a expanded view of the FIG. 2 prosthesis.

Referring now to the drawings, it will be understood that the showings therein are intended to teach a preferred embodiment of the present invention but are not intended to limit the invention thereto.

The spring wire prosthesis of the present invention is intended to be surgically placed between the tympanic membrane and the stapes footplate to provide an otic reconstruction in situations where the malleus handle is still present as well as situations where the malleus handle is lacking.

Turning now to the particular situation where the malleus handle is still attached to the tympanic membrane, the FIG. 1 embodiment shows that the spring wire prosthesis of the present invention can be mounted so as to connect the malleus handle directly to the footplate. To accomplish this the closed end loop 22 is pressed against one side of the malleus handle while a sharp protruding tip 30 extending from the loop 23 is pressed into the other side thus effectively capturing malleus handle. The purpose of the loop 23 is to allow for the surgeon to insert an instrument therein which will flex the prosthesis while positioning it under the malleus handle. This member 8 is connected to an oval shaped spring assembly 14 by an arm 10. The oval shaped spring assembly 14 is aligned between° the tympanic membrane and the footplate so as to have the major axis or diameter 21 substantially parallel to the tympanic membrane when the prosthesis in place and is properly compressed. This ensures that the spring will have sufficient clearance between the promontory and the tympanic membrane preventing any short circuiting of the wire spring prosthesis. To provide additional springiness to the prosthesis while maintaining its compact size an additional coil 24 is formed to be substantially circular and to have a diameter that is substantially equal to the minor axis or diameter 29 of the oval spring assembly 14.

A leg 20 extends from the spring assembly 14 terminating in a circular member 26 having a sharp tip 28 which is placed on the footplate in the oval window. The coil 26 presses against the footplate to distribute the force of the prosthesis and to prevent the sharp tip 28 from dislodging from the footplate. With the prosthesis in place as shown in FIG. 1, the prosthesis assembly is compressed approximately 1 millimeter. Thus, any type of external trauma is now easily absorbed by the spring assembly 14 rather than causing an extrusion of the prosthesis through the oval window into the inner ear. Similarly, any space re-orientation due to healing is also compensated by the spring assembly 14. A further benefit of the oval shape of the spring assembly providing the clearance within the elements of the middle ear to the spring assembly 14 ensures that any shift of the individual middle ear members due to healing or other causes will not cause a short circuit of the prosthesis. Thus is will be seen that no matter what the material of the spring wire prosthesis, it is clearly beneficial to form the spring assembly as an oval and align the major diameter 21 of the oval in a parallel direction with the tympanic membrane and enclose the oval spring assembly 14 within the enclosed angle formed by said legs 10 and 20. This location is maintained for all the modified prosthesis discussed later to ensure sufficient clearance between the tympanic membrane and the promotory while providing sufficient springiness to accommodate the mentioned variations.

To ensure that the prosthesis has great inherent flexibility while maintaining compactness and tensile strength, the Applicant has found that forming the prosthesis from a plurality of individual wire strands allows for these added benefits.

Figure 8:
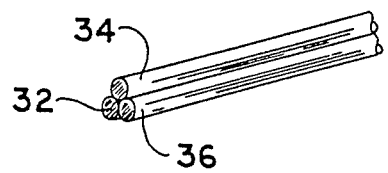
FIG. 8 shows the three individual wire strands before they are twisted into a unitary member.
Figure 9:
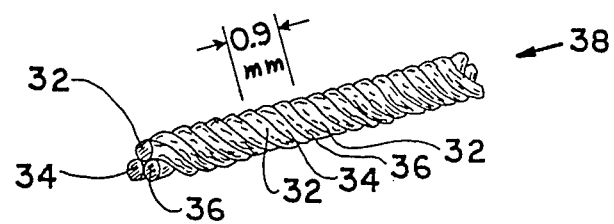
FIG. 9 shows a cutaway section of the FIG. 8 wires after they have been twisted into a unitary section.
Figure 10:
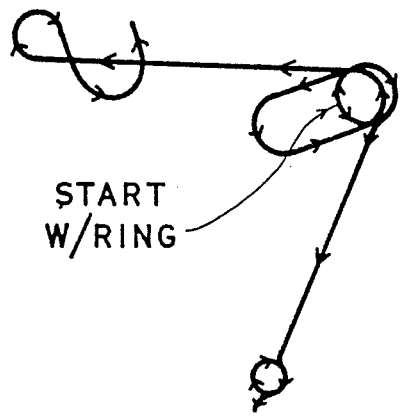
FIG. 10 schematically depicts the particular way to FIG. 7 prosthesis is formed by following the direction of the arrows.

With particular reference to FIGS. 8-10, it will be seen that three identical wires 32, 34, and 36 are twisted together to form a cable assembly 38. Each of the wires 32, 34 and 36 are type 316LVM (low carbon vacuum melt) stainless steel wires (ASTM Specification F-138-86) having an individual diameter of 0.0026 inches. When twisted together as shown in FIG. 9, they form a cable assembly 38 having a diameter of approximately 0.0055 inches. The tensile strength of this cable was measured to be between 130,000 psi and 140,000 psi. The twisting of the assembly was done to the point where a space of between 0.9 and approximately 1 millimeter millimeters existed between repetitions of an individual strand. This is clearly depicted in FIG. 9.

Once the cable assembly 38 is formed, the prosthesis is twisted into the shape seen in the remaining Figures by forming it as per the arrow diagram in FIG. 10. The forming of the individual loops is apparent when following the direction of the arrows starting at the indicated START point on the circular loop and extending in opposite directions.

This particular cable assembly 38 formed spring wire prosethesis was found by the Applicant to have superior flexibility and high tensile strength which allows for an compact prosthesis making it easy for the surgeon to implant and ensures that sufficient clearances are maintained between the walls and elements of the middle ear to ensure that no short circuiting of the prosthesis will occur.

Turning now to FIGS. 2-5, it will be seen that the present prosthesis may also be used to connect the footplate to the tympanic membrane in situations where the malleus handle is not present.

Figure 4:
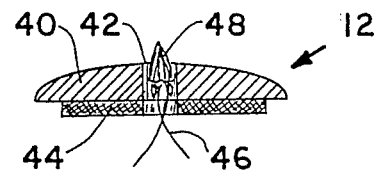
FIG. 4 shows an enlarged side view of the member used to mount the FIG. 3 prosthesis against the tympanic membrane.
Figure 5:
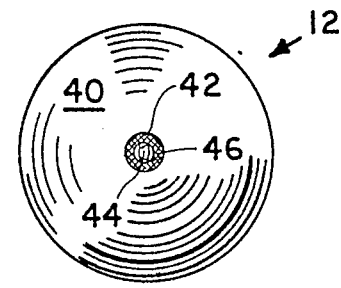
FIG. 5 shows a top view of the FIG. 4 member.
Figure 6:
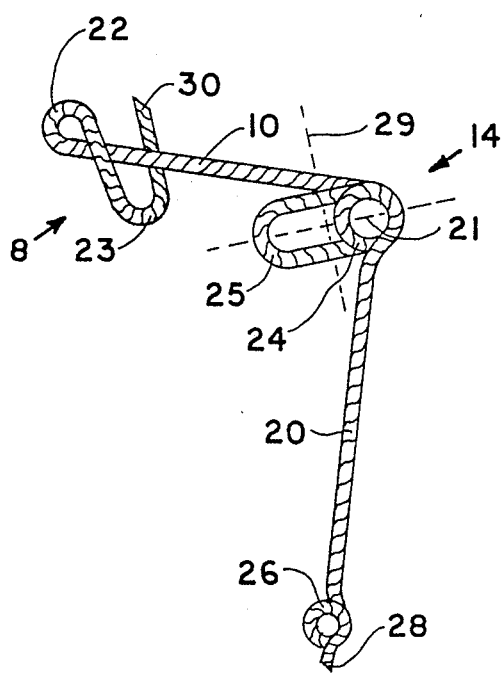
FIG. 6 shows an expanded view of the FIG. 1 prosthesis.
Figure 7:
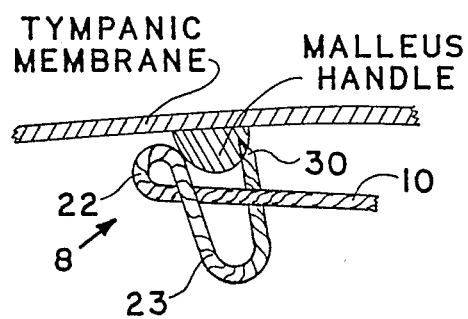
FIG. 7 shows an expanded view of the ampersand shaped end of the FIG. 1 prosthesis capluring the malleus handle therein.

To accomplish this the prosthesis as shown in FIG. 1 and 6–10 is modified by eliminating and the section 23 from the ampersand shaped assembly 8 to the tip of the wire 18 is now extending forward to limit excess rotations of the assembly 12. The remaining loop 22 is connected to a disc assembly 12 made of a bio-compatible material such as Hydroxyapatite. The assembly 12 is composed of the mentioned biocompatible material formed into a disc member 40 having a central aperature 42. The disc 40 is glued to a wire mesh platform 44. The wire mesh platform allows the assembly 12 to be tied loosely to the closed end loop 22 by way of a thin wire platform 46 extending through the central portion of the platform 44 as shown in FIG. 4. This allows the assembly 12 to be flexibly connected to the prosthesis or to be freely mobile floating therefrom thus allowing it to easily conform to occurring positional variances of the tympanic membrane by equally distributing pressure to the undersurface of the tympanic membrane, diminishes the conditions causing pressure necrosis and extrusion. To ensure that the assembly 12 does not slide along and off the tympanic membrane a bone chip 48 is embedded into the central aperture 42 of the assembly 12.

The particular details of the surgical implantation of such wire devices into the middle ear are clearly explained in the Applicant's previous U.S. Pat. No. 4,624,672 which was referred to in the description of the prior art. Hence, this description will not be repeated herein but is incorporated by reference to said previous patent to which the reader is referred.

Certain modifications and improvements have been deleted herein for the sake of conciseness and readability but are clearly intended to fall within the scope of the following claims. As an example, surgical base material such as cartiledge or perycondrium could be added to the head of the prosthesis and the prosthesis implanted as a unit under the tympanic membrane. Similarly, although twisted wire has been disclosed, braided wire could also have been used after determining empirical compensating factors between such twisted and braided wires.

I claim:

1. A prosthesis for ossicular reconstruction mountable between the tympanic membrane and the footplate of the middle ear comprising:

a spring means;
   a lower arm having one end connected to the spring means and a second end having means for connection to the footplate;
   an upper arm having one end connected to the spring means and a second end having means for connection to the tympanic membrane;
   said upper and lower arms defining a plane and forming an enclosed angle therebetween; and
   said spring means including an oval coil oriented substantially parallel to said plane and substantially within the enclosed angle thereby minimizing contact of the coiled spring means with the walls of the middle ear.

2. A prosthesis as set forth in claim 1 wherein said spring means further including a circular coil.

3. A prosthesis as set forth in claim 1 wherein said second end of said upper arm includes biocompatible material affixed thereto wherein said biocompatible material is biased against the tympanic membrane by said spring means.

4. A prosthesis as set forth in claim 3 wherein said biocompatible material has a bone chip located thereon for retaining said material to the tympanic membrane by lodging of the bone chip into the tympanic membrane.

5. A prosthesis as set forth in claim 3 wherein said biocompatible material is tied to a loop means formed at said second end of the upper arm by a tying means.

6. A prosthesis as set forth in claim 5 wherein said wire loop means includes an ampersand shaped wire having an open side and an extended leg formed at the end of the open side of the ampersand shaped wire to allow the malleus handle to be located between the extended leg and the open side of the ampersand shaped wire to connect the prosthesis to the malleus handle thereby.

7. A prosthesis as set forth in claim 5 wherein said biocompatible material is formed from a biocompatible ceramic.

8. A prosthesis as set forth in claim 5 including a wire mesh platform affixed to said disc member.

9. A prosthesis as set forth in claim 8 wherein said tying means includes a thin wire tying said wire mesh platform and the wire loop means together to make the disc member loosely connected to the wire loop means of the prosthesis thereby.

10. A wire prosthesis for ossicular reconstruction mountable between the tympanic membrane and the footplate of the middle ear comprising:

a spring means;
    a lower arm having one end connected to the spring means and a second end having means for connection to the footplate;
    an upper arm having one end connected to the spring means and a second end having means for connection to the tympanic membrane;
    said upper and lower arms and said spring means being formed from a plurality of wire strands twisted together to form a single unitary wire spring assembly, wherein said upper and lower arms define a plane and form an enclosed angle therebetween; and
    said spring means including an oval coil oriented substantially parallel to said plane and substantially within the enclosed angle thereby minimizing contact of the coiled spring means with the walls of the middle ear.

11. A wire prosthesis as set forth in claim 10 wherein said wire strands are Type 316LVM stainless steel.

12. A wire prosthesis as set forth in claim 11 wherein said spring means further including a circular coil having a diameter substantially the same as the minor diameter of the oval.

13. A wire prosthesis as set forth in claim 10 wherein said wire spring assembly is formed from three wire strands twisted together to have a diameter of approximately 0.0055 inches.

* * * * *